United States Patent
Kim et al.

(10) Patent No.: US 9,262,823 B2
(45) Date of Patent: Feb. 16, 2016

(54) MEDICAL IMAGE GENERATING APPARATUS AND MEDICAL IMAGE GENERATING METHOD

(71) Applicant: SAMSUNG MEDISON CO., LTD., Gangwon-do (KR)

(72) Inventors: Han Jun Kim, Seoul (KR); Sung Yun Kim, Namyangju-si (KR); Jun Sang Yoo, Suwon-si (KR); Jun Kyo Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 123 days.

(21) Appl. No.: 14/084,140

(22) Filed: Nov. 19, 2013

(65) Prior Publication Data
US 2014/0139526 A1    May 22, 2014

(30) Foreign Application Priority Data
Nov. 19, 2012    (KR) .................. 10-2012-0130802

(51) Int. Cl.
| | | |
|---|---|---|
| *G06T 7/00* | (2006.01) | |
| *G06T 15/08* | (2011.01) | |
| *H04N 13/02* | (2006.01) | |
| *H04N 13/00* | (2006.01) | |
| *H04N 13/04* | (2006.01) | |
| *A61B 8/08* | (2006.01) | |
| *A61B 8/00* | (2006.01) | |

(52) U.S. Cl.
CPC .............. *G06T 7/0012* (2013.01); *A61B 8/466* (2013.01); *A61B 8/483* (2013.01); *G06T 15/08* (2013.01); *H04N 13/0022* (2013.01); *H04N 13/0275* (2013.01); *H04N 13/0278* (2013.01); *H04N 13/0475* (2013.01); *A61B 8/4405* (2013.01)

(58) Field of Classification Search
None
See application file for complete search history.

(56) References Cited

U.S. PATENT DOCUMENTS

| | | |
|---|---|---|
| 5,840,034 A | 11/1998 | Amemiya et al. |
| 2009/0147074 A1 | 6/2009 | Getty |
| 2010/0030079 A1 | 2/2010 | Hamada |
| 2012/0026158 A1 | 2/2012 | Oto |

FOREIGN PATENT DOCUMENTS

| | | |
|---|---|---|
| JP | 09-299364 A | 11/1997 |
| JP | 2000-005166 A | 1/2000 |
| JP | 2001-161693 A | 6/2001 |
| WO | 96-22660 A1 | 7/1996 |
| WO | 2004-061544 A2 | 7/2004 |
| WO | 2012-164430 A2 | 12/2012 |

OTHER PUBLICATIONS

Extended European Search Report issued in corresponding European Application No. 13190561.4, dated Jul. 14, 2014.

*Primary Examiner* — Zhengxi Liu
(74) *Attorney, Agent, or Firm* — McDermott Will & Emery LLP

(57) ABSTRACT

A 3D ultrasound image generating apparatus and method includes a volume-data generator to generate 3-dimensional (3D) volume data based on at least one cross-sectional image with respect to a body tissue of a subject, and a controller that generates the final 3D image having the adjusted 3D effect by volume rendering the 3D volume data based on the input stereo-depth value when a stereo-depth value used to adjust the 3D effect of a final 3D image generated based on the 3D volume data is input.

22 Claims, 15 Drawing Sheets

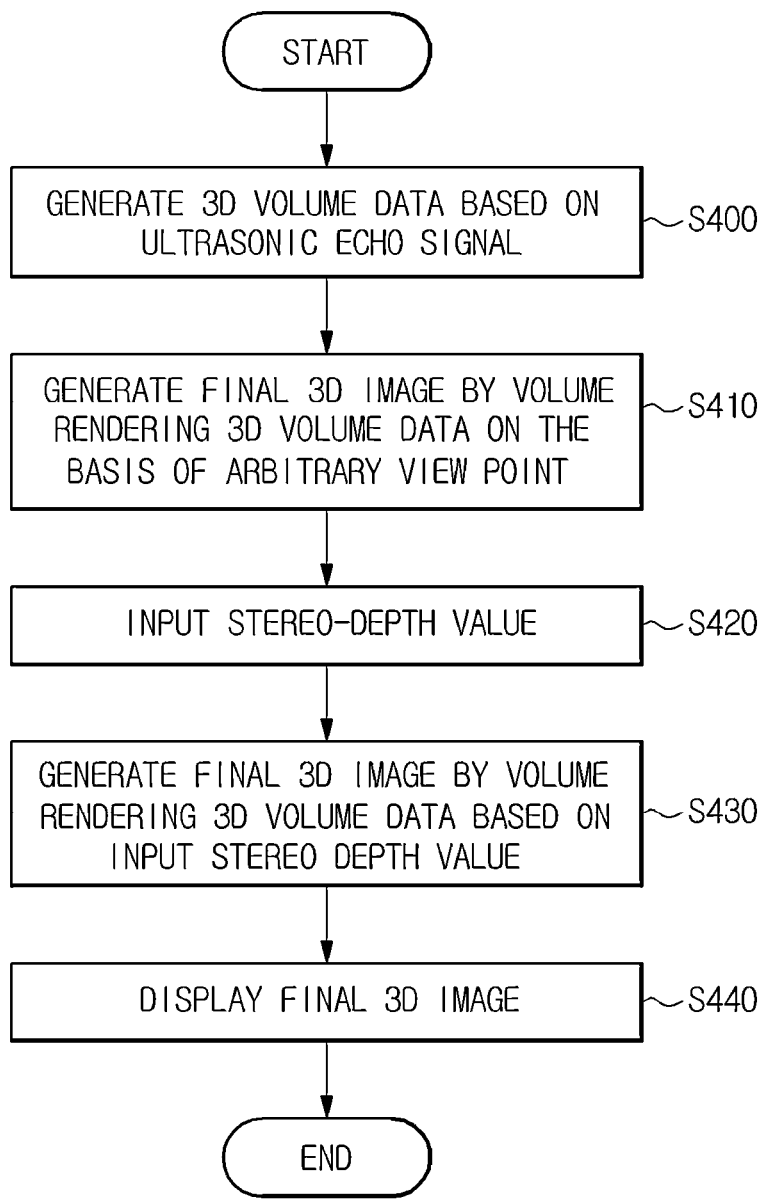

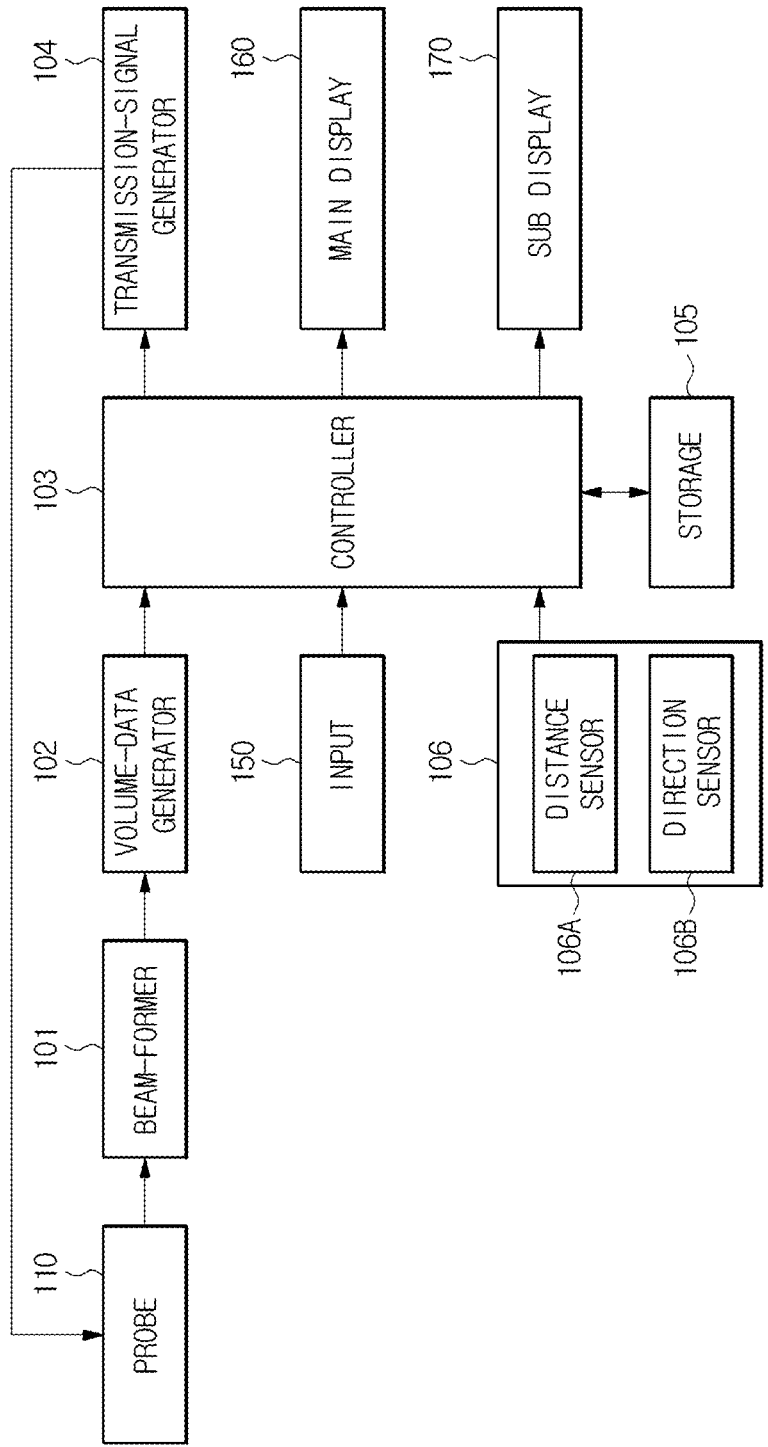

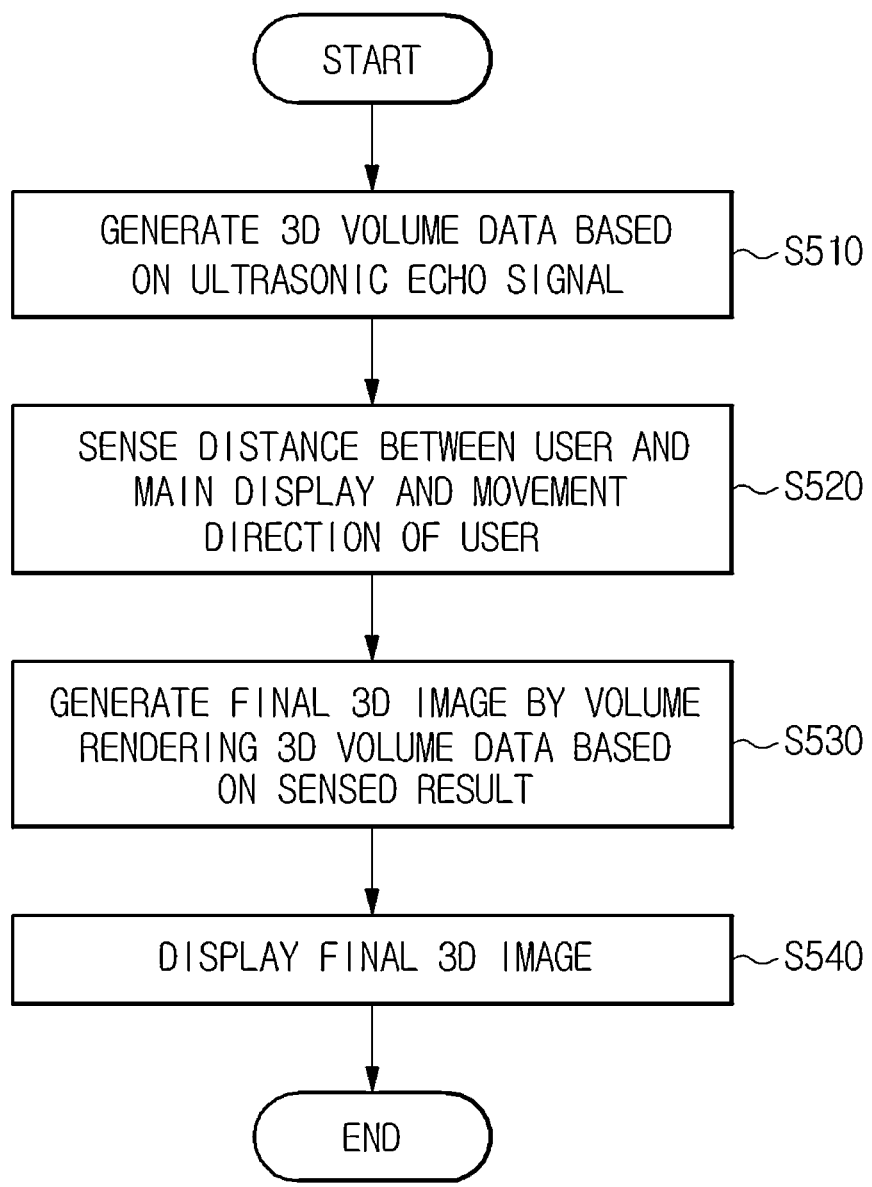

MEDICAL IMAGE GENERATING APPARATUS AND MEDICAL IMAGE GENERATING METHOD

CROSS-REFERENCE TO RELATED APPLICATION

This application claims the benefit of Korean Patent Applications No. 10-2012-0130802, filed on Nov. 19, 2012 in the Korean Intellectual Property Office, the disclosure of which is incorporated herein by reference.

BACKGROUND

1. Technical Field

Embodiments of the present disclosure relate to a 3-Dimensional (3D) medical image generating apparatus and method which enable adjustment in the 3D effect and spatial effect of a medical image.

2. Background

Studies of medical image appliances are actively underway with an increased interest in healthcare. Examples of medical image appliances may include an X-ray imaging apparatus, X-ray fluoroscopy apparatus, Computerized Tomography (CT) scanner, Magnetic Resonance Imaging (MRI) apparatus, Positron Emission Tomography (PET) apparatus, and ultrasonic diagnostic apparatus.

The medical image appliances display a 2D medical image, 3D medical image, 3D stereoscopic medical image, or the like.

A medical image appliance to display a 3D stereoscopic medical image generates a left image corresponding to the left eye of a viewer and a right image corresponding to the right eye, and displays the left and right images simultaneously. The viewer may view a 3D stereoscopic medical image by wearing, e.g., 3D stereoscopic glasses.

The left image and the right image are generated based on a distance between human left and right eyes. That is, the left image and right image are generated under the assumption that the distance between human left and right eyes is 6.5 cm.

The aforementioned data on the distance between human left and right eyes is statistically obtained data. Thus, when left and right images are simultaneously displayed on a display, the 3D effect and spatial effect of a resulting 3D stereoscopic medical image may differ for each viewer, and some viewers may suffer from dizziness when viewing the 3D stereoscopic medical image. Also, it may be necessary for a viewer to maintain a predetermined distance from the display to easily view the 3D stereoscopic medical image, which may restrict the viewer's movement.

SUMMARY

It is an aspect of the present disclosure to provide a medical image generating apparatus and method which enable adjustment in the 3D effect and spatial effect of a 3D medical image.

Additional aspects of the disclosure will be set forth in part in the description which follows and, in part, will be obvious from the description, or may be learned by practice of the disclosure.

In accordance with one aspect of the disclosure, a medical image generating apparatus includes a volume-data generator configured to generate 3-Dimensional (3D) volume data based on at least one cross-sectional image with respect to a body tissue of a subject, and a controller configured to generate a final 3D image having an adjusted 3D effect by volume rendering the 3D volume data based on the input stereo-depth value when a stereo-depth value used to adjust the 3D effect of the final 3D image generated based on the 3D volume data is input.

The medical image generating apparatus may further include a display configured to display a user interface including an icon used to set the stereo-depth value.

The icon may include a scroll bar, and at least one button configured to adjust the stereo-depth value may be provided around the scroll bar.

The stereo-depth value may be adjusted via selection of the at least one button.

The stereo-depth value may be adjusted via selection of a predetermined position on the scroll bar.

The controller may be configured to generate a single 3D medical image by volume rending the 3D volume data on the basis of a predetermined view point if the input stereo-depth value is zero.

The controller may be configured to determine a rotation angle with respect to the 3D volume data based on the input stereo-depth value when the input stereo-depth value is greater than zero, generate at least two 3D medical images by volume rendering the 3D volume data on the basis of a predetermined view point and a view point rotated by the rotation angle from the predetermined view point, and generate a 3D stereoscopic medical image by combining the generated two 3D medical images.

The rotation angle may be proportional to the input stereo-depth value.

The medical image generating apparatus may further include a sensor configured to sense a distance between a display and a user.

The input stereo-depth value may be set based on the distance sensed by the sensor.

The medical image generating apparatus may further include a sensor configured to sense a movement direction of a user from a reference position of a display, and the reference position may be a position perpendicular to a display screen of the display.

The controller may be configured to rotate the 3D volume data in an opposite direction of the direction sensed by the sensor, and then perform volume rendering of the 3D volume data based on the input stereo-depth value.

In accordance with another aspect of the present disclosure, a medical image generating method includes generating 3D volume data based on at least one cross-sectional image with respect to a body tissue of a subject, receiving a stereo-depth value to adjust the 3D effect of a final 3D image generated based on the 3D volume data, and generating the final 3D image having the adjusted 3D effect by volume rendering the 3D volume data based on the input stereo-depth value.

The medical image generating method may further include displaying a user interface including an icon used to set the stereo-depth value.

The icon may include a scroll bar, and at least one button to adjust the stereo-depth value may be provided around the scroll bar.

The stereo-depth value may be adjusted via selection of the at least one button.

The stereo-depth value may be adjusted via selection of a predetermined position on the scroll bar.

Generation of the final 3D image may include generating a single 3D medical image by volume rending the 3D volume data on the basis of a predetermined view point if the input stereo-depth value is zero.

Generation of the final 3D image may include determining a rotation angle with respect to the 3D volume data based on the input stereo-depth value if the input stereo-depth value is greater than zero, generating at least two 3D medical images by volume rendering the 3D volume data on the basis of a predetermined view point and a view point rotated by the rotation angle from the predetermined view point, and generating a 3D stereoscopic medical image by combining the generated two 3D medical images.

The rotation angle may be proportional to the input stereo-depth value.

The medical image generating method may further include sensing a distance between a display and a user.

The input stereo-depth value may be set based on the sensed distance.

The medical image generating method may further include sensing a movement direction of a user from a reference position of a display, and the reference position may be a position perpendicular to a display screen of the display.

Generation of the final 3D image may include rotating the 3D volume data in an opposite direction of the sensed direction, and performing volume rendering of the 3D volume data based on the input stereo-depth value, so as to generate at least one 3D medical image.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 8 is a flowchart illustrating a 3D ultrasound image generating method performed by the ultrasound image generating apparatus of FIG. 3;

FIG. 9 is a block diagram illustrating a control configuration of a 3D ultrasound image generating apparatus according to another embodiment of the present disclosure; and FIG. 10 is a flowchart illustrating a 3D ultrasound image generating method according to another embodiment of the present disclosure.

DETAILED DESCRIPTION

Figure 1:
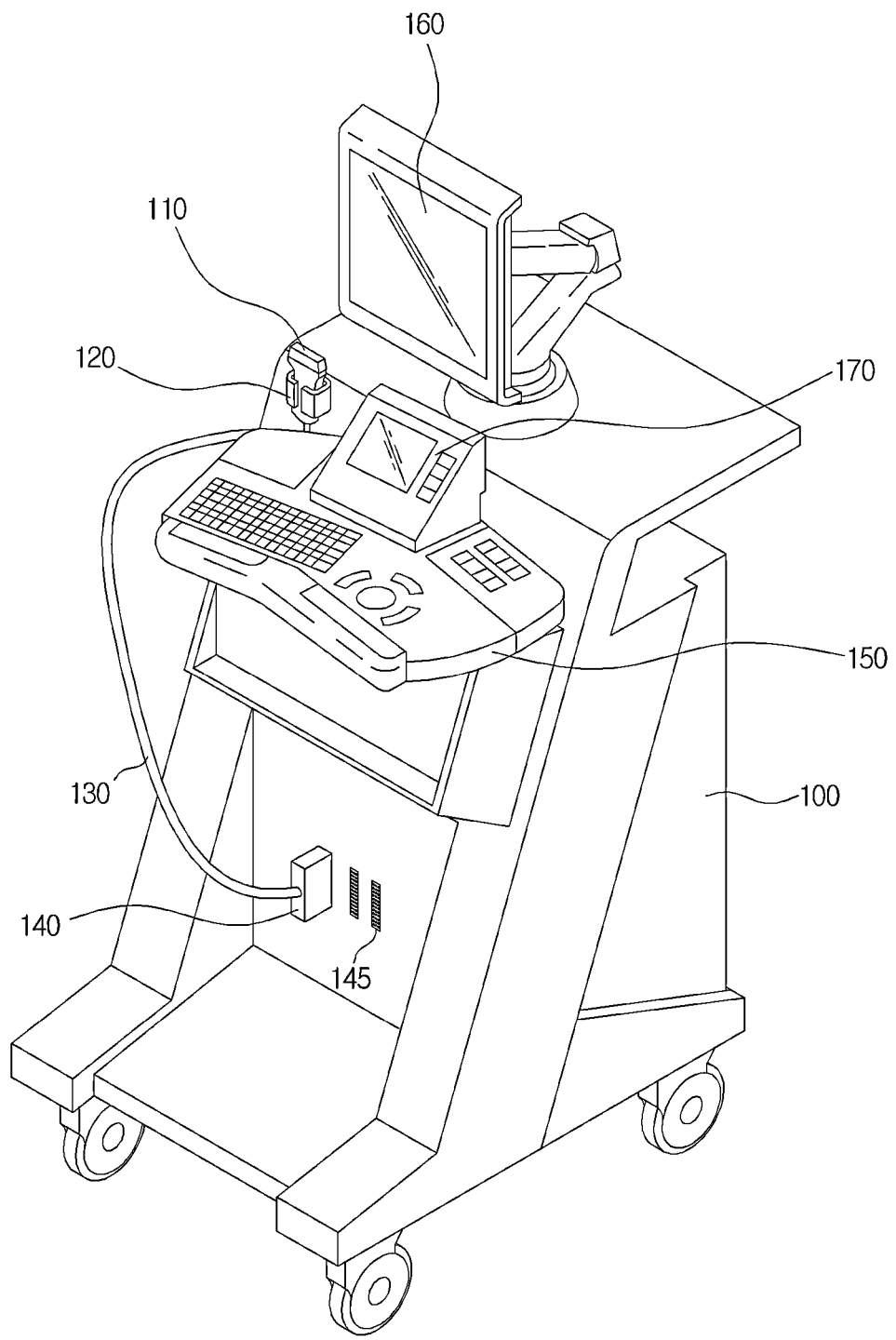
FIG. 1 is a perspective view illustrating an external appearance of an ultrasound image generating apparatus according to an embodiment of the present disclosure.

The advantages and features of the present disclosure and the way of attaining them will become apparent with reference to embodiments described below in detail in conjunction with the accompanying drawings. Embodiments, however, may be embodied in many different forms and should not be constructed as being limited to example embodiments set forth herein. Rather, these example embodiments are provided so that this disclosure will be thorough and complete. The scope of the present disclosure should be defined by the claims.

Reference will now be made in detail to the embodiments of the present disclosure, examples of which are illustrated in the accompanying drawings, wherein like reference numerals refer to like elements throughout.

A medical image generating apparatus according to the embodiments of the present disclosure may refer to any one of an X-ray imaging apparatus, X-ray fluoroscopy apparatus, CT scanner, MRI apparatus, PET apparatus, and ultrasonic diagnostic apparatus. In the following description, for convenience, the case in which a medical image generating apparatus is an ultrasonic diagnostic apparatus will be described by way of example.

FIG. 1 is a perspective view illustrating an external appearance of an ultrasound image generating apparatus according to an embodiment of the present disclosure. As illustrated in FIG. 1, the ultrasound image generating apparatus may include a main body 100, a probe 110, an input 150, a main display 160, and a sub display 170.

Figure 3:
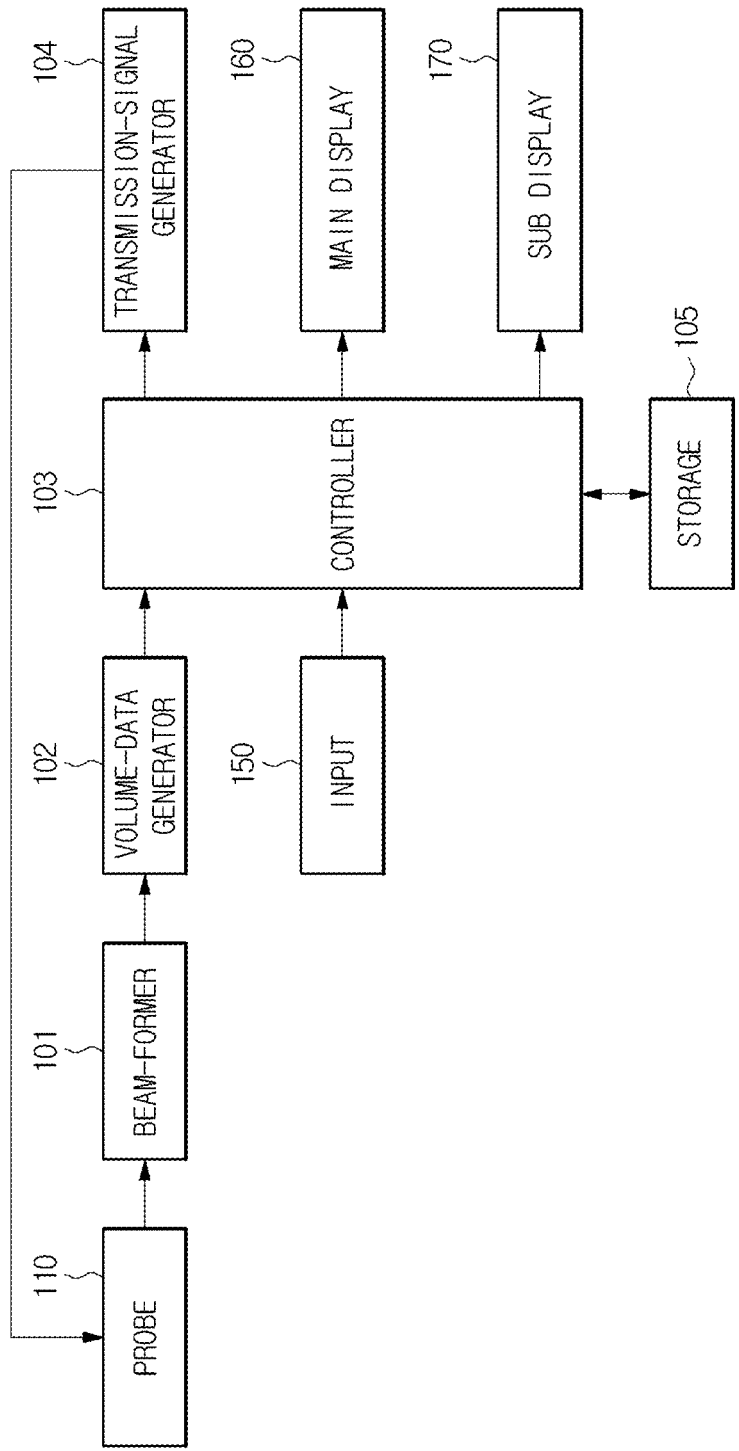
FIG. 3 is a block diagram illustrating a control configuration of the ultrasound image generating apparatus according to one embodiment of the present disclosure.

The main body 100 may accommodate main constituent elements of the ultrasound image generating apparatus, for example, a transmission-signal generator (see 104 in FIG. 3). If a user inputs an ultrasonic diagnosis instruction, the transmission-signal generator 104 may generate a transmission-signal and transmit the transmission-signal to the probe 110.

More than one female connector 145 may be provided at one side of the main body 100. A male connector 140 connected to a cable 130 may be physically coupled to the female connector 145. The transmission-signal generated by the transmission-signal generator 104 may be transmitted to the probe 110 by way of the male connector 140 connected to the female connector 145 of the main body 100 and the cable 130.

To provide mobility of the ultrasound image generating apparatus, a plurality of casters may be provided at the bottom of the main body 100. The plurality of casters may fix the ultrasound image generating apparatus at a particular place, or may allow the ultrasound image generating apparatus to be moved in a particular direction.

The probe 110 may be configured to come into contact with the body surface of a subject (for example, the abdomen of the mother) and function to transmit and receive an ultrasonic signal. More specifically, the probe 110 may serve to direct the transmission-signal received from the main body 100, i.e. an ultrasonic signal into the human body of the subject, and to receive an ultrasonic echo signal reflected from a particular object (for example, the fetus) within the human body of the subject so as to transmit the ultrasonic echo signal to the main body 100. One end of the cable 130 may be connected to the probe 110 and the other end of the cable 130 may be connected to the male connector 140. The male connector 140 connected to the other end of the cable 130 may be physically coupled to the female connector 145 of the main body 100.

The input 150 may receive an instruction related to operation of the ultrasound image generating apparatus. For example, the input 150 may receive an instruction to select a mode, such as an A-mode (Amplitude mode), B-mode (Brightness mode), and M-mode (Motion mode), an ultrasonic diagnosis initiation instruction, and a stereo-depth value to adjust the 3D effect and spatial effect of a final 3D image.

The input 150 may include, for example, at least one of a touchpad, keyboard, foot switch, and foot pedal. The touchpad or keyboard may be a hardware element located at an upper position of the main body 100. The keyboard may include at least one of switches, keys, wheels, joysticks, trackballs, and knobs. In another example, the keyboard may be a software element, such as a graphical user interface. In this case, the keyboard may be displayed via at least one of the sub display 170 and the main display 160. The foot switch or foot pedal may be provided at a lower position of the main body 100 to assist the user (an operator) in controlling operation of the ultrasound image generating apparatus.

An instruction input via the input 150 may be transmitted to the main body 100 via wired or wireless communication. More specifically, if the input 150 is provided at a remote controller or 3D stereoscopic glasses, the instruction input via the input 150 may be transmitted to the main body 100 via wireless communication.

A probe holder 120 in which the probe 110 is placed may be provided near the input 150. More than one probe holder 120 may be provided. The user may place the probe 110 in the probe holder 120 for storage when the ultrasound image generating apparatus is not in use.

The sub display 170 may be provided at the main body 100. FIG. 1 illustrates the case in which the sub display 170 is located above the input 150. The sub display 170 may display applications related to operation of the ultrasound image generating apparatus. For example, the sub display 170 may display, e.g., a menu or guide map required for ultrasonic diagnosis. The sub display 170, for example, may take the form of a Cathode Ray Tube (CRT) or a Liquid Crystal Display (LCD). The sub display 170 may be omitted. In this case, the applications or menu displayed via the sub display 170 may be displayed via the main display 160 that will be described hereinafter.

The main display 160 may be provided at the main body 100. FIG. 1 illustrates the case in which the main display 160 is located above the sub display 170. The main display 160 may be a CRT or LCD, similar to the sub display 170. Although FIG. 1 illustrates the main display 160 as being coupled to the main body 100, the main display 160 may be separable from the main body 100. The main display 160 may display a user interface related to ultrasonic diagnosis. The user interface may include a menu to adjust the 3D effect and spatial effect of the final 3D image. Here, a more detailed description of the user interface will be given with reference to FIG. 2.

Figure 2:
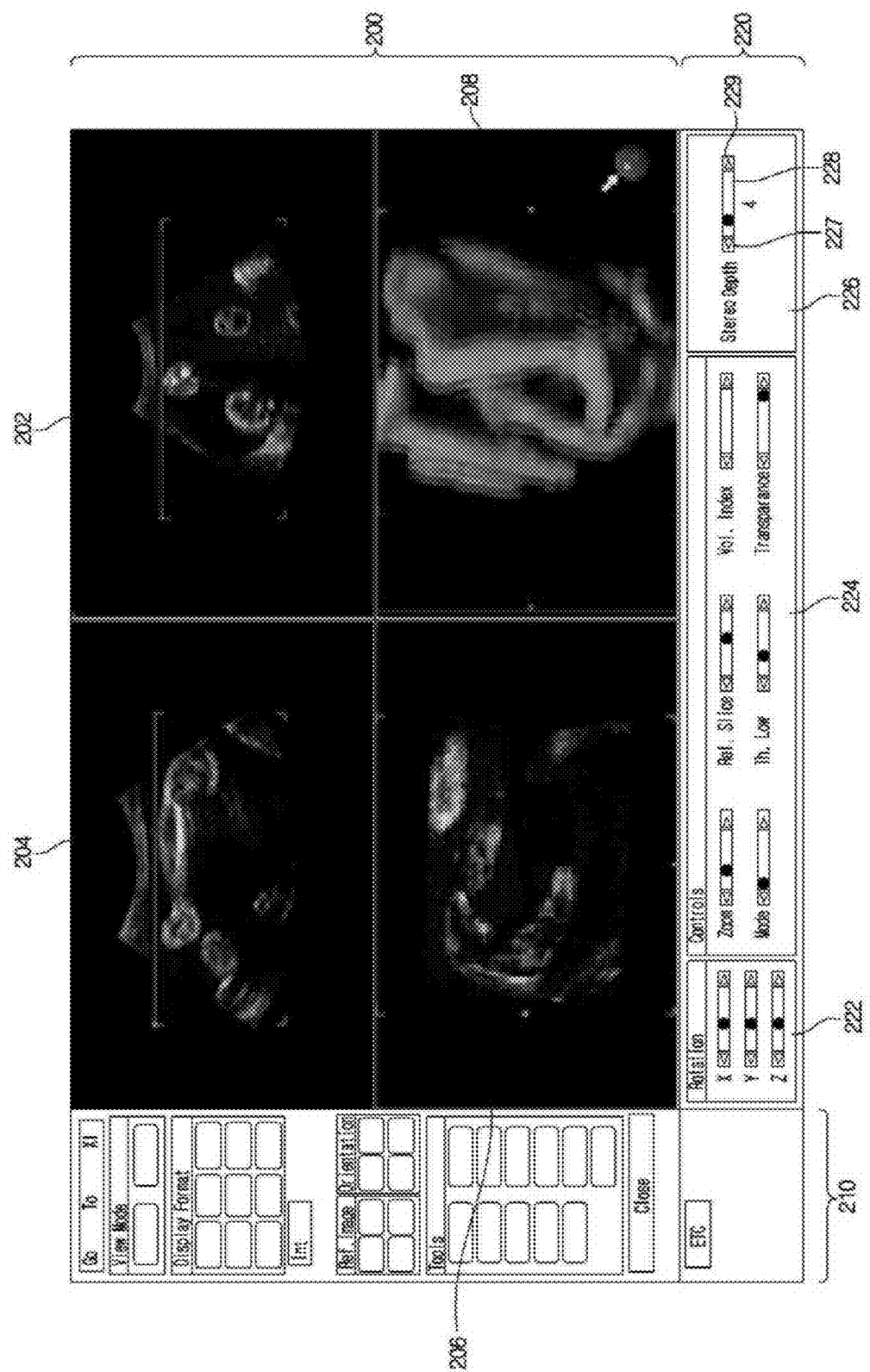
FIG. 2 is a view illustrating a user interface displayed via a main display of FIG. 1.

FIG. 2 is a view illustrating a user interface according to an embodiment of the present disclosure.

As illustrated in FIG. 2, the user interface may include an image display area 200, a first menu display area 210, and a second menu display area 220.

The image display area 200 is an area where at least one ultrasound image acquired via ultrasonic diagnosis is displayed. Referring to FIG. 2, it will be appreciated that the image display area 200 is divided into quadrants. Hereinafter, starting from an upper right quadrant, a first quadrant 202, a second quadrant 204, a third quadrant 206, and a fourth quadrant 208 are sequentially arranged in a counterclockwise direction.

A final 3D image acquired by ultrasonic diagnosis may be displayed in the fourth quadrant 208. In this case, the final 3D image displayed in the fourth quadrant 208 may be a 3D ultrasound image or 3D stereoscopic ultrasound image. Here, the 3D ultrasound image is a black-and-white or color image acquired by volume rendering volume data based on a single view point. That is, the 3D ultrasound image refers to a 2D projected image on 3D volume data. On the other hand, the 3D stereoscopic ultrasound image refers to a black-and-white or color image acquired by generating a left image and a right image via volume rendering of volume data based on two view points that respectively correspond to human left and right eyes, and combining the generated images.

An X-axis cross-sectional image for the final 3D image may be displayed in the first quadrant 202. A Y-axis cross-sectional image for the final 3D image may be displayed in the second quadrant 204. Also, a Z-axis cross-sectional image for the final 3D image may be displayed in the third quadrant 206.

Icons used to select various setting values required for ultrasonic diagnosis may be displayed in the first menu display area 210. The first menu display area 210 may be located at a left vertical side of the user interface.

Icons used to select various setting values related to the final 3D image may be displayed in the second menu display area 220. For example, at least one icon used to set a rotation angle on the basis of each of three axes (X-axis, Y-axis and Z-axis) may be displayed in a partial area 222 of the second menu display area 220. Also, icons used to adjust various control values, such as the transparency of the final 3D image, the number of volume rendering times, etc., may be displayed in another area 224 of the second menu display area 220.

Additionally, an icon used to adjust the 3D effect and spatial effect of the final 3D image may be displayed in the other area 226 of the second menu display area 220. The 3D effect and spatial effect of the final 3D image may be achieved by adjusting a stereo-depth value of volume data.

FIG. 2 illustrates the case in which the icon to adjust a stereo-depth value takes the form of a scroll bar 228. One or more buttons 227 and 229 to adjust a stereo-depth value may be provided around the scroll bar 228. In FIG. 2, the button 227 to reduce the stereo-depth value and the button 229 to increase the stereo-depth value are respectively provided at both ends of the scroll bar 228. However, the disclosure is not limited thereto, and both the buttons 227 and 229 may be provided at the left side or right side of the scroll bar 228.

The user may reduce the stereo-depth value by clicking the button 227 provided at the left end of the scroll bar 228, and may increase the stereo-depth value by clicking the button 229 provided at the right end of the scroll bar 228. Alternatively, a desired stereo-depth value may be input by clicking a particular position of the scroll bar 228.

The stereo-depth value may be reduced or increased by 1 whenever the button 227 provided at the left end of the scroll bar 228 or the button 229 provided at the right end is clicked once. In another example, the stereo-depth value may be reduced or increased by 2 whenever the left button 227 or the right button 229 is clicked once. An interval of the stereo-depth value that is reduced or increased whenever the button is clicked once may be preset, or may be set by the user. In this case, the user interface of FIG. 2 may further display a menu or icon to set a change interval of the stereo-depth value.

For example, stereo-depth values from zero to 10 may be mapped in the scroll bar 228. If the stereo-depth value is zero, the fourth quadrant 208 of the image display area 200 may display a 3D ultrasound image as the final 3D image. If the stereo-depth value is not zero, the fourth quadrant 208 may display a 3D stereoscopic ultrasound image as the final 3D image.

As described above, the 3D ultrasound image is a black-and-white or color image acquired by volume rendering volume data based on a single view point. Also, the 3D stereoscopic ultrasound image is a black-and-white or color image acquired by generating left and right images via volume rendering of volume data based on two view points, and combining the acquired images. The 3D effect of the 3D stereoscopic ultrasound image is changed based on the input stereo-depth value. A more detailed description thereof will be given with reference to FIGS. 7A to 7F.

A currently selected stereo-depth value may be numerically displayed at a lower end of the scroll bar 228. In the case of FIG. 2, it will be appreciated that the numeral '4' is displayed at the lower end of the scroll bar 228. This means that the stereo-depth value, i.e. the 3D effect of the 3D ultrasound image is set to '4'.

Referring again to FIG. 1, a plurality of ultrasonic transducers (not shown) to generate ultrasonic waves in response to an electric signal may be provided at a distal end of the probe 110.

The ultrasonic transducers may generate ultrasonic waves upon receiving AC power. More specifically, the ultrasonic transducers may receive AC power from an external power supply device or an internal charge device, for example, a battery. The ultrasonic waves may be generated as piezoelectric oscillators or thin films of the ultrasonic transducers oscillate upon receiving AC power.

The ultrasonic transducers, for example, may be selected from among various kinds of ultrasonic transducers, such as magnetostrictive ultrasonic transducers using the magnetostrictive effect of a magnetic substance, piezoelectric ultrasonic transducers using the piezoelectric effect of a piezoelectric material, and a capacitive micro-machined ultrasonic transducers that transmit and receive ultrasonic waves using vibration of several hundreds or several thousands of micro-machined thin films.

The ultrasonic transducers may constitute a linear or curvilinear array. A cover (not shown) to cover the ultrasonic transducers may be provided over the ultrasonic transducers.

The external appearance of the ultrasound image generating apparatus according to the embodiment of the present disclosure has been described above. Hereinafter, an embodiment of the ultrasound image generating apparatus and method will be described in more detail with reference to FIGS. 3 to 8.

FIG. 3 is a block diagram illustrating a control configuration of the ultrasound image generating apparatus according to the embodiment of the present disclosure.

As illustrated in FIG. 3, the ultrasound image generating apparatus may include a transmission-signal generator 104, probe 110, beam-former 101, volume-data generator 102, controller 103, input 150, storage 105, main display 160, and sub display 170.

Of the aforementioned constituent elements, the input 150, the main display 160, and the sub display 170 have been described with reference to FIG. 1, and a repeated description thereof will be omitted.

The transmission-signal generator 104 may generate a transmission signal in consideration of positions and a focusing point of the ultrasonic transducers. Here, the transmission signal refers to a high-pressure electric signal to oscillate the ultrasonic transducers. The generated transmission signal may be transmitted to the ultrasonic transducers of the probe 110.

The ultrasonic transducers of the probe 110 may change the transmission signal to an ultrasonic signal, direct the ultrasonic signal to the subject, and receive an ultrasonic echo signal from the subject. The received ultrasonic echo signal may be transmitted to the beam-former 101.

Figure 4:
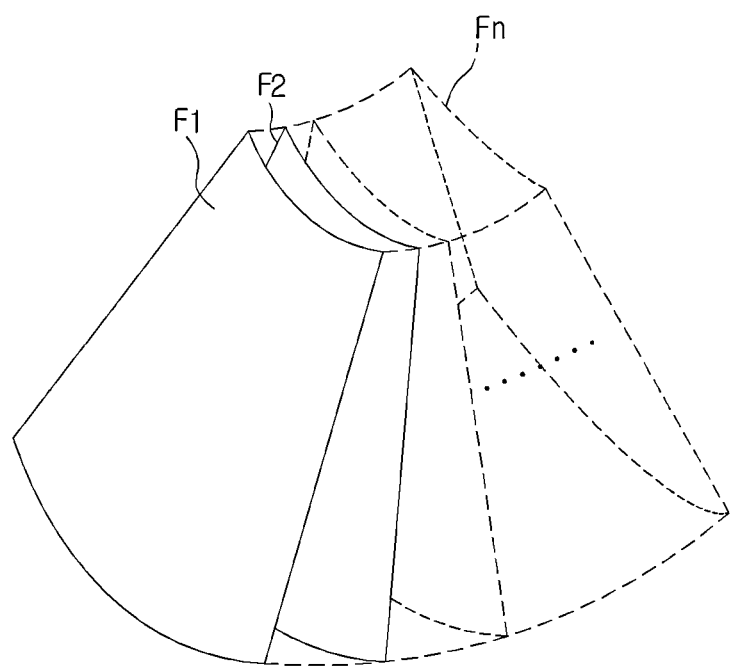
FIG. 4 is a view illustrating a plurality of cross-sectional images.

The beam-former 101 may change the analog ultrasonic echo signal into a digital signal. Additionally, the beam-former 101 may apply a time delay to the digital signal in consideration of the positions and focusing point of the ultrasonic transducers. Then, the beam-former 101 may focus the received digital signal to generate a focused signal. The focused signal generated by the beam-former 101 may be understood as cross-sectional images F1, F2, . . . , Fn of the subject. A plurality of cross-sectional images may be generated as illustrated in FIG. 4.

Figure 5:
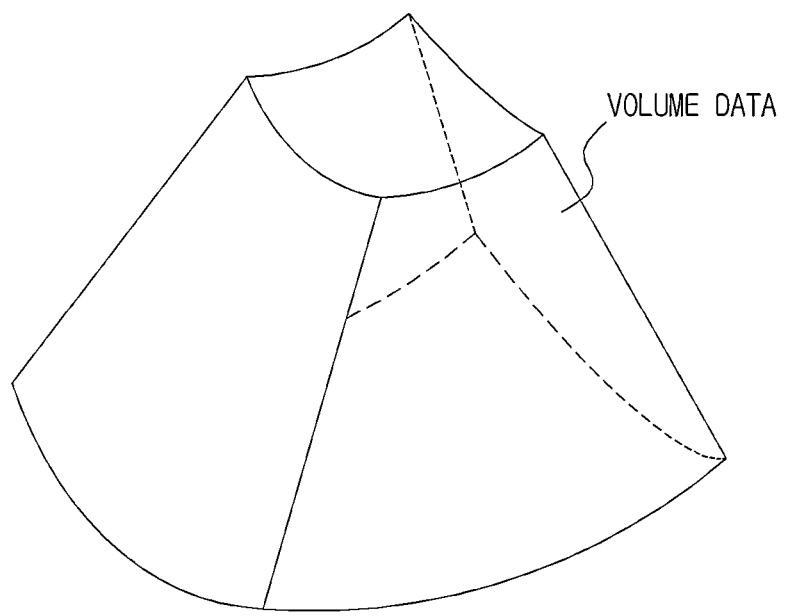
FIG. 5 is a view illustrating volume data.

The volume-data generator 102 may generate 3D volume data on the subject based on the plurality of cross-sectional images F1, F2, . . . , Fn generated by the beam-former 101, as illustrated in FIG. 5. The volume data may be represented by a plurality of voxels. The term "voxel" is formed through combination of the terms "volume" and "pixel". While pixel refers to a single point in a 2D space, voxel refers to a single point in a 3D space. A pixel has X- and Y-coordinates, whereas a voxel has X-, Y-, and Z-coordinates.

The controller 103 may constitute the user interface as illustrated in FIG. 2. The controller 103 may generate the final 3D image by volume rendering 3D volume data based on the stereo-depth value input via the user interface or the input 150. If the stereo-depth value is zero, the final 3D image generated by the controller 103 is a 3D ultrasound image. If the stereo-depth value is not zero, the final 3D image generated by the controller 103 is a 3D stereoscopic ultrasound image.

The controller 103 may perform volume rendering of 3D volume data using one of conventional known volume rendering methods. The volume rendering may be classified into surface rendering and direct volume rendering.

Surface rendering is a method including extracting surface information from volume data based on a constant scalar value and spatial variation, and changing the extracted surface information into a geometrical element, such as a polygonal or curvilinear patch, to apply a conventional rendering method thereto. Examples of surface rendering may include a marching cubes algorithm and a dividing cubes algorithm.

Direct volume rendering is a method for direct rending of volume data without an intermediate process of changing volume data into a geometrical element. The direct volume rendering may directly provide visual information on the interior of an object and may be advantageous to display a semi-transparent structure. The direct volume rendering may be classified into an object-order method and an image-order method based on a method of accessing volume data.

The image-order method is a method to determine pixel values of an image sequentially. One example of the image-order method includes Ray-Casting. Here, the concept of Ray-Casting will be described in brief with reference to FIG. 6.

Figure 6:
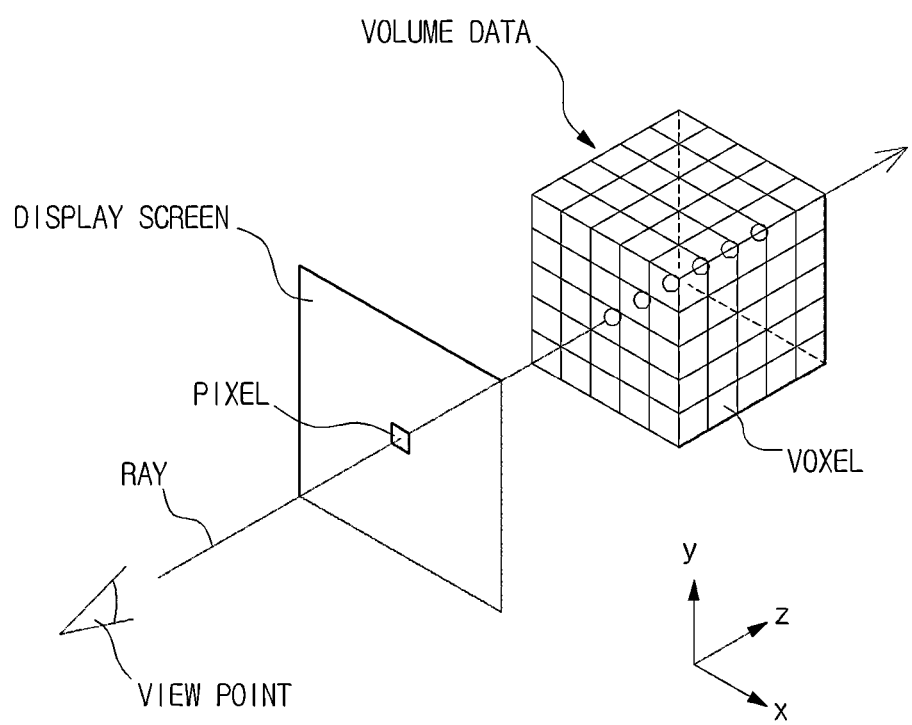
FIG. 6 is an explanatory view of volume rendering.
Figure 7:
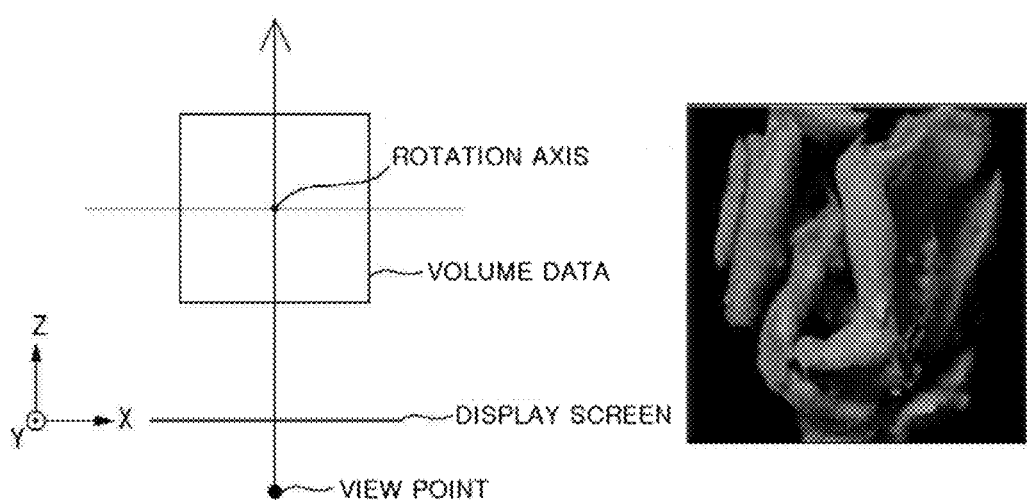
FIGS. 7A to 7F are views illustrating a rotation angle of the volume data and a final 3D image depending on a stereo-depth value.
Figure 7:
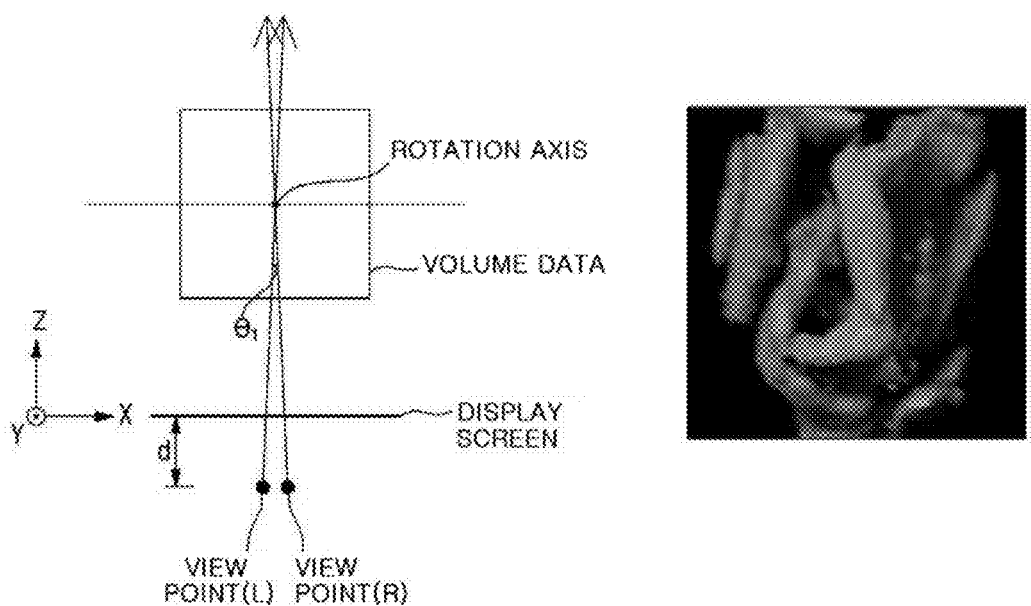
Figure 7:
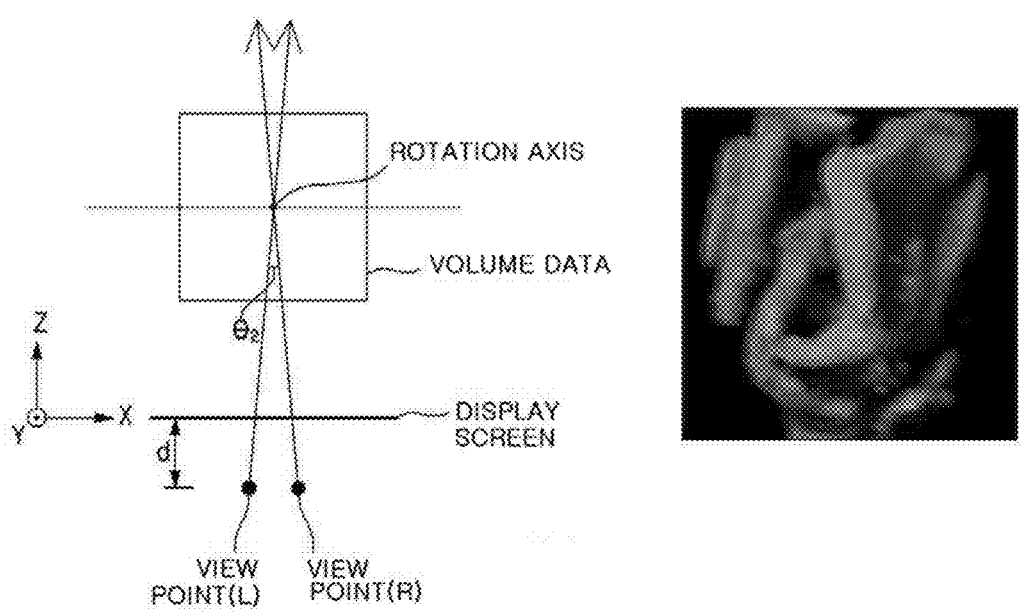
Figure 7:
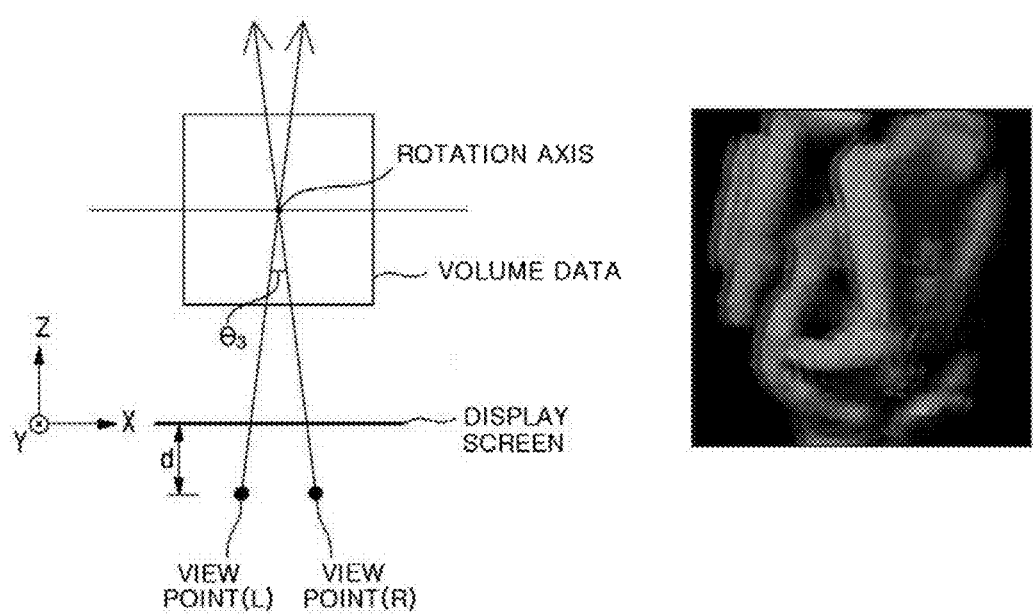
Figure 7:
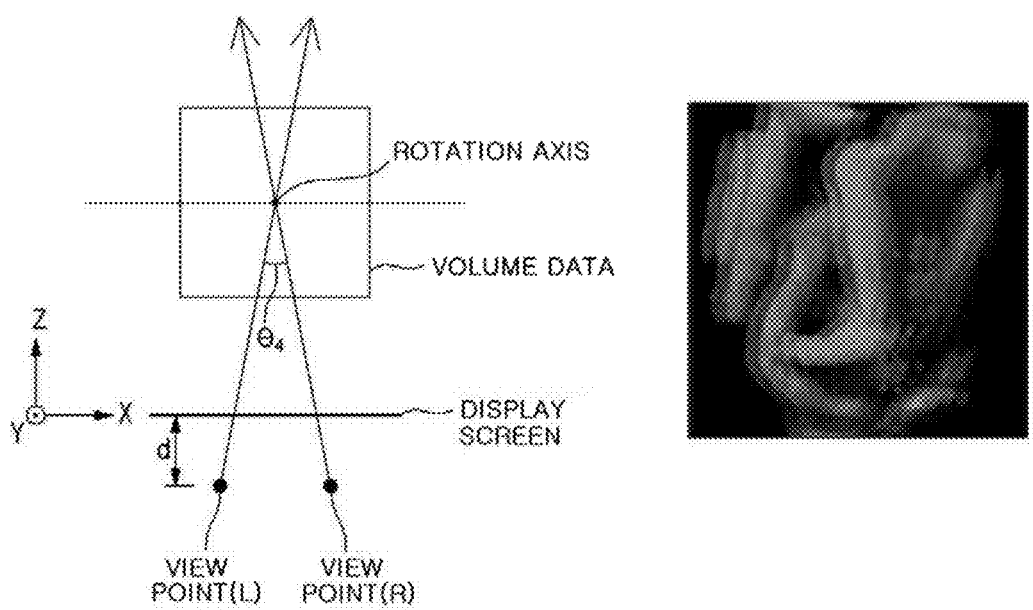
Figure 7:
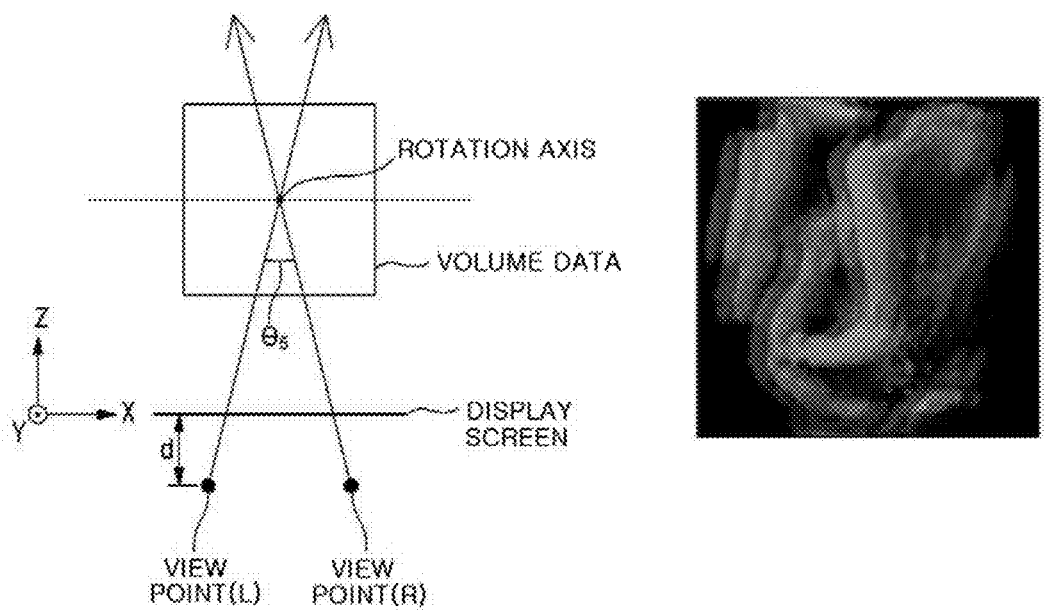

Ray-casting, as illustrated in FIG. 6, includes emitting a virtual ray from a view point to a predetermined pixel of a display screen, and detecting some voxels of volume data through which the ray passes. Then, a brightness value of the corresponding pixel is determined by accumulating brightness values of the detected voxels.

In addition to the above-described volume rendering methods, the controller 103 may use Ray-Tracing. Here, Ray-Tracing is a method to find light entering the observer's eyes by tracing ray paths one by one.

Once volume rendering has been completed based on the stereo-depth value, at least one 3D ultrasound image may be generated. The 3D ultrasound image is a 2D projected image with respect to 3D volume data.

The number of 3D ultrasound images generated via volume rendering may be changed based on the input stereo-depth value.

For example, if the input stereo-depth value is zero, the controller 103 may generate a single 3D ultrasound image by volume rendering 3D volume data from a predetermined view point. In this case, the view point may be preset by the user.

If the input stereo-depth value is greater than zero, the controller 103 may generate at least two 3D ultrasound images including a left image and a right image. More specifically, the controller 103 acquires a left image (or a right image) by volume rendering volume data from a predetermined view point, and then acquires a right image (or a left image) by repeatedly performing volume rendering from a view point that is rotated by a predetermined angle from the initial view point. In this case, the rotation angle with respect to the volume data may be determined based on the stereo-depth value. A more detailed description thereof will follow with reference to FIGS. 7A to 7F.

FIGS. 7A to 7F are views illustrating a rotation angle of volume data and a final 3D image depending on a stereo-depth value. More specifically, FIGS. 7A to 7F illustrate rotation angles of volume data and final 3D images respectively when stereo-depth values are 0, 2, 4, 6, 8, and 10.

In FIGS. 7A to 7F, the left drawing illustrates the volume data of FIG. 6 with respect to an X-Z plane, and the right drawing illustrates a final 3D image resulting from volume rendering.

As illustrated in FIG. 7A, if the stereo-depth value is zero, volume rendering is performed on the basis of a predetermined view point. It will be appreciated that a single 3D ultrasound image is generated via volume rendering.

As illustrated in FIGS. 7B to 7F, if the stereo-depth value is not zero (i.e. if the stereo-depth value is greater than zero), volume rendering is performed at a predetermined view point L and a view point R rotated by angles $\theta_1$, $\theta_2$, $\theta_3$, $\theta_4$, or $\theta_5$, from the view point L. By combining a left image and a right image acquired by volume rendering, a 3D stereoscopic ultrasound image is generated. As illustrated in FIGS. 7B to 7F, rotation of the view point is performed on the basis of a rotation axis. FIGS. 7B to 7F illustrate the case in which the rotation axis is located at the center of volume data, and a position of the rotation axis may be displaced along a Z-axis. In this case, the user interface of FIG. 2 may further include a menu or icon to adjust the position of the rotation axis.

Referring to FIGS. 7B to 7F, it will be appreciated that the rotation angle of the volume data may be increased ($\theta_1 < \theta_2 < \theta_3 < \theta_4 < \theta_5$) as the stereo-depth value is increased from 2 to 10. Also, it will be appreciated that the 3D effect of a 3D stereoscopic ultrasound image is changed as the rotation angle is increased.

Referring again to FIG. 3, the storage 105 may store data or algorithms required to operate the ultrasound image generating apparatus. For example, the storage 105 may store an algorithm to generate volume data based on a plurality of cross-sectional images, an algorithm for rendering of volume data, and a lookup table representing a mapping relationship between the rotation angle of volume data and the stereo-depth value.

The storage 105 may take the form of a storage medium including a non-volatile memory, such as Read Only Memory (ROM), Programmable Read Only Memory (PROM), Erasable Programmable Read Only Memory (EPROM), and a flash memory, volatile memory device such as Random Access Memory (RAM), a hard disc, or an optical disc. However, it will be appreciated that the disclosure is not limited to the above examples and the storage 105 may have other shapes known in the art.

FIG. 8 is a flowchart illustrating an ultrasound image generating method according to an embodiment of the present disclosure.

If ultrasonic diagnosis is initiated, the operator brings the probe 110 into contact with the abdomen of the mother. Thereby, an ultrasonic signal is directed from the probe 110 to the abdomen of the mother, and the probe 110 receives an ultrasonic echo signal reflected from a subject, for example, the fetus within the abdomen. 3D volume data may be generated based on the received ultrasonic echo signal (S400). Generation of the 3D volume data may include changing the analog ultrasonic echo signal into a digital signal, focusing the received digital signal to generate a plurality of focused signals, and generating 3D volume data on the subject based on the plurality of focused signals.

Once the 3D volume data has been generated, volume rendering is performed with respect to an arbitrary view point, to generate a final 3D image (S410). One example of volume rendering used may include surface rending or direct volume rendering. The final image generated in Operation S410 may be a 3D ultrasound image or a 3D stereoscopic ultrasound image. The final 3D image generated may be displayed in the image display area 200 of the user interface illustrated in FIG. 2. For example, the final 3D image may be displayed in the fourth quadrant 208 of the image display area 200. The first quadrant 202, the second quadrant 204, and the third quadrant 206 may respectively display an X-axis cross-sectional image, a Y-axis cross-sectional image, and a Z-axis cross-sectional image with respect to the final 3D image. In such a state, the operator may adjust a generation position of each axis cross-sectional image by operating the input 150, such as a mouse, etc.

Once the final 3D image on the basis of the arbitrary view point is displayed, the operator may input a stereo-depth value (S420). More specifically, the operator may set a desired stereo-depth value by clicking, at least one time, one of the buttons 227 and 229 provided at both ends of the scroll bar 228 of the user interface as illustrated in FIG. 2. Alternatively, the operator may set a desired value by selecting a particular position of the scroll bar 228.

Clicking one of the buttons 227 and 229 provided at both ends of the scroll bar 228 or selecting the particular position of the scroll bar 228 may be performed as the operator operates, e.g., keys or buttons provide at the keyboard, mouse, remote controller, or 3D stereoscopic glasses. If the main display 160 is a touchscreen, the operator may directly click one of the buttons 227 and 229 provided at both ends of the scroll bar 228 with the finger, or may directly select the particular position of the scroll bar 228 with the finger.

Once the stereo depth value has been input, a final 3D image may be generated via volume rendering of volume data based on the input stereo-depth value (S430). The final 3D image generated may be a 3D ultrasound image, or 3D stereoscopic ultrasound image.

More specifically, if the input stereo-depth value is zero, as illustrated in FIG. 7A, volume rendering is performed on the basis of a single view point. As a result, a single 3D ultrasound image is generated as the final 3D image.

If the input stereo-depth value is not zero, for example, if the input stereo-depth value is greater than zero, as illustrated in FIGS. 7B to 7F, volume rendering is performed on the basis of two view points. That is, a 3D ultrasound image is acquired by performing volume rendering on the basis of a predetermined view point. Subsequently, 3D ultrasound image is acquired by repeatedly performing volume rendering on the basis of a view point rotated by an angle corresponding to the stereo-depth value. By combining the acquired two 3D ultrasound images, a 3D stereoscopic ultrasound image is generated.

The final 3D image generated in the above-described manner may be displayed in the image display area 200 of the user interface (S440). For example, the final 3D image may be displayed in the fourth quadrant 208 of the image display area 200.

Description has been given of the ultrasound image generating method according to the embodiment of the present disclosure. FIG. 8 illustrates the case in which the final 3D image is generated by volume rendering 3D volume data on the basis of an arbitrary view point (S410), and the generated final 3D image is displayed to allow the operator to adjust the stereo-depth value after checking the final 3D image. However, the step of generating the final 3D image by volume rendering 3D volume data on the basis of an arbitrary view point (S410) may not be essential, and may be omitted as occasion demands.

The order of the respective operations illustrated in FIG. 8 may be changed. For example, receiving the stereo-depth value (S420) may be performed before generating 3D volume data based on ultrasonic echo signals (S400), or may be performed between generating 3D volume data based on ultrasonic echo signals (S400) and the step of generating the final 3D image by volume rendering 3D volume data on the basis of an arbitrary view point (S410).

Next, an ultrasound image generating apparatus and method according to another embodiment of the present disclosure will be described with reference to FIGS. 9 and 10.

FIG. 9 is a block diagram illustrating a control configuration of an ultrasound image generating apparatus according to another embodiment of the present disclosure.

As illustrated in FIG. 9, the ultrasound image generating apparatus may include the transmission-signal generator 104, probe 110, beam-former 101, volume-data generator 102, controller 103, input 150, storage 105, sensor 106, main display 160 and sub display 170.

Of the constituent elements illustrated in FIG. 9, the probe 110, beam-former 101, volume-data generator 102, input 150, transmission-signal generator 104, main display 160, sub-display 170, and storage 105 have been described above with reference to FIGS. 1 and 3, and thus a repeated description thereof will be omitted. The following description is focused on only differences.

The ultrasound image generating apparatus illustrated in FIG. 9 may further include a sensor 106, unlike the ultrasound image generating apparatus illustrated in FIG. 3.

The sensor 106 may include at least one of a distance sensor 106A and a direction sensor 106B.

The distance sensor 106A may sense a distance between the operator and the display, for example, the main display 160. The distance sensor 106A, for example, may include at least one of an infrared sensor and a depth sensor (not shown).

The direction sensor 106B may sense a movement direction of the operator from a reference position of the display, for example, the main display 160. That is, the direction sensor 106B may sense a movement direction and movement distance of the operator from a reference position.

Here, the reference position is a position perpendicular to the display screen of the main display 160. FIG. 6 illustrates the case in which the view point, i.e. the operator, is located at the reference position. Although the operator may be located at the reference position during implementation of ultrasonic diagnosis, the operator may deviate from the reference position as occasion demands. For example, the operator may move leftward, rightward, upward or downward by a predetermined angle from the reference position.

To sense a movement direction and movement length of the operator from the reference position, the direction sensor 106B may include a camera to capture an image of the front side of the main display 160, an algorithm to detect a human, or human eyes, from an image acquired via the camera, and an algorithm to calculate a movement direction and movement distance of the operator from the reference position based on a position of the detected human, or human eyes.

The controller 103 may perform volume rendering of 3D volume data based on the sensed result of the sensor 106.

More specifically, the controller 103 may perform volume rendering after rotating the volume data in an opposite direction or other direction of the movement direction of the operator from the reference position.

Also, the controller 103 may set the stereo-depth value based on the distance between the operator and the main display 160, and perform volume rendering based on the set stereo-depth value. To this end, the controller 103 may refer a reference distance d. The reference distance d may be stored in the storage 105.

For example, if the distance between the user and the main display 160 is less than the reference distance d, the stereo-depth value may be set to zero. If the stereo-depth value is zero, a single 3D ultrasound image may be generated.

If the distance between the user and the main display 160 is equal to or greater than the reference distance d, the stereo-depth value may be set in proportion to the sensed distance. Also, volume rendering may be performed based on the set stereo-depth value. If the stereo-depth value is not zero, volume rendering is performed at two view points, and consequently at least two 3D ultrasound images, for example, the left and right images, may be generated. Then, the controller 103 may generate a 3D stereoscopic ultrasound image by combining the two 3D ultrasound images.

FIG. 10 is a flowchart illustrating a 3D ultrasound image generating method according to another embodiment of the present disclosure.

If ultrasonic diagnosis is initiated, the operator brings the probe 110 into contact with the abdomen of the mother. Thereby, an ultrasonic signal is directed from the probe 110 to the abdomen of the mother, and the probe 110 receives an ultrasonic echo signal reflected from a subject within the abdomen. As such, 3D volume data may be generated based on the received ultrasonic echo signal (S510). Generation of the 3D volume data may include changing the analog ultrasonic echo signal into a digital signal, focusing the received digital signal to generate a plurality of focused signals, and generating 3D volume data on the subject based on the plurality of focused signals.

Thereafter, the distance between the operator and the main display 160 and the movement direction of the operator from the reference position may be sensed (S520). The sensing of the distance between the operator and the main display 160 and the movement direction of the operator from the reference position may be performed by the sensor 106.

Thereafter, a final 3D image may be generated by volume rendering 3D volume data based on the sensed results (S530). The generation of the final 3D image S530 may include rotating volume data in an opposite direction or other direction of the movement direction of the operator from the reference position, setting a stereo-depth value in proportion to the distance between the operator and the main display 160, and volume rendering the volume data based on the set stereo-depth value.

The final 3D image generated may be a 3D ultrasound image or a 3D stereoscopic ultrasound image. More specifically, if the stereo-depth value set based on the distance between the operator and the main display 160 is zero, a single 3D ultrasound image may be generated as a final image. If the stereo-depth value set based on the distance between the operator and the main display 160 is greater than zero, volume rending is performed on the basis of two view points, and consequently at least two 3D ultrasound images, for example, the left and right images, may be generated. By combining the acquired at least two 3D ultrasound images, a 3D stereoscopic ultrasound image may be generated as a final image.

The final 3D image generated by volume rendering may be displayed via the main display 160 (S540). In another example, the final 3D image may be transmitted to an external device (not shown) located at a remote place via wired or wireless communication, and may be displayed via a display connected to the external device.

Description has been given of the embodiments of the present disclosure. In addition to the above-described embodiments, the embodiments of the present disclosure may be realized via a medium including computer readable code/instruction to control at least one processing element of the above-described embodiments, for example, a computer readable medium. The medium may correspond to a medium/media that enables storage and/or transmission of the computer readable code.

The computer readable code may also be transmitted via the Internet. The medium, for example, may include a recording medium, such as a magnetic storage medium (e.g., a ROM, floppy disc, and hard disk) and an optical recording medium (e.g., a CD-ROM or DVD), and a transmission medium such as carrier waves. According to the embodiment of the present disclosure, the medium may be a signal, such as a complex signal or bitstream. The medium may further include a distributed network, and therefore the computer readable code may be stored, transmitted, and executed in a distributed manner. Moreover, the processing element may include a processor or computer processor by way of example. The processing element may be distributed and/or included in a single device.

As is apparent from the above description, with the medical image generating apparatus and method according to the embodiments, the following effects are obtained.

Adjustment ability in the 3D effect and spatial effect of a 3D medical image may improve user satisfaction.

It may not be essential to maintain a reference distance between an operator and a display, which increases user convenience.

Although the embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A medical image generating apparatus comprising:
 a volume-data generator to generate 3-Dimensional (3D) volume data based on at least one cross-sectional image with respect to a body tissue of a subject; and
 a controller configured to
 determine a rotation angle which corresponds to a stereo-depth value when the stereo-depth value is input,
 determine the rotation angle with respect to the 3D volume data based on the input stereo-depth value if the input stereo-depth value is greater than zero,
 generate two 3D medical images by volume rendering the 3D volume data on the basis of a predetermined view point and a view point rotated by the rotation angle from the predetermined view point, and
 generate a 3D stereoscopic medical image by combining the two generated 3D medical images,
 wherein the rotation angle is determined based on the input stereo-depth value.

2. The apparatus according to claim 1, further comprising a display configured to display a user interface including an icon used to set the stereo-depth value.

3. The apparatus according to claim 2, wherein the icon includes a scroll bar, and at least one button configured to adjust the stereo-depth value is provided around the scroll bar.

4. The apparatus according to claim 3, wherein the stereo-depth value is configured to be adjusted via selection of the at least one button.

5. The apparatus according to claim 3, wherein the stereo-depth value is configured to be adjusted via selection of a predetermined position on the scroll bar.

6. The apparatus according to claim 1, wherein the controller is configured to generate a single 3D medical image by volume rending the 3D volume data on the basis of a predetermined view point when the input stereo-depth value is zero.

7. The apparatus according to claim 1, wherein the rotation angle is proportional to the input stereo-depth value.

8. The apparatus according to claim 1, further comprising a sensor configured to sense a distance between a display and a user.

9. The apparatus according to claim 8, wherein the input stereo-depth value is configured to be set based on the distance sensed by the sensor.

10. The apparatus according to claim 1, further comprising a sensor configured to sense a movement direction of a user from a reference position of a display,
 wherein the reference position is a position perpendicular to a display screen of the display.

11. The apparatus according to claim 10, wherein the controller is configured to rotate the 3D volume data depending on the direction sensed by the sensor, and then perform volume rendering of the 3D volume data based on the input stereo-depth value.

12. A medical image generating method comprising:
 generating 3D volume data based on at least one cross-sectional image with respect to a body tissue of a subject;
 receiving a stereo-depth value;
 determining a rotation angle which corresponds to the received stereo-depth value;
 determining the rotation angle with respect to the 3D volume data based on the received stereo-depth value if the received stereo-depth value is greater than zero;
 generating two 3D medical images by volume rendering the 3D volume data on the basis of a predetermined view point and a view point rotated by the rotation angle from the predetermined view point; and
 generating a 3D stereoscopic medical image by combining the two generated 3D medical images,
 wherein the rotation angle is determined based on the received stereo-depth value.

13. The method according to claim 12, further comprising displaying a user interface including an icon used to set the stereo-depth value.

14. The method according to claim 13, wherein the icon includes a scroll bar, and at least one button to adjust the stereo-depth value is provided around the scroll bar.

15. The method according to claim 14, wherein the stereo-depth value is adjusted via selection of the at least one button.

16. The method according to claim 14, wherein the stereo-depth value is adjusted via selection of a predetermined position on the scroll bar.

17. The method according to claim 12, wherein generation of the 3D stereoscopic medical image includes generating a single 3D medical image by volume rending the 3D volume data on the basis of a predetermined view point if the received stereo-depth value is zero.

18. The method according to claim 12, wherein the rotation angle is proportional to the received stereo-depth value.

19. The method according to claim 12, further comprising sensing a distance between a display and a user.

20. The method according to claim 19, wherein the input stereo-depth value is set based on the sensed distance.

21. The method according to claim 12, further comprising sensing a movement direction of a user from a reference position of a display,
  wherein the reference position is a position perpendicular to a display screen of the display.

22. The method according to claim 21, wherein generation of the 3D stereoscopic medical image includes:
  rotating the 3D volume data depending on the sensed direction; and
  performing volume rendering of the 3D volume data based on the received stereo-depth value, so as to generate at least one 3D medical image.

* * * * *